United States Patent [19]
Yasuda et al.

[11] Patent Number: 5,936,098
[45] Date of Patent: Aug. 10, 1999

[54] PROCESS FOR PRODUCING INDOLINE COMPOUNDS AND INTERMEDIATES FOR THE PRODUCTION OF THE SAME

[75] Inventors: Nobuyuki Yasuda; Shin-ichi Kunii; Kouichi Kazama, all of Tokyo, Japan

[73] Assignee: Tokyo Tanabe Company Limited, Tokyo, Japan

[21] Appl. No.: 08/894,855

[22] PCT Filed: Feb. 16, 1996

[86] PCT No.: PCT/JP96/00344

§ 371 Date: Aug. 14, 1997

§ 102(e) Date: Aug. 14, 1997

[87] PCT Pub. No.: WO96/25396

PCT Pub. Date: Aug. 22, 1996

[30] Foreign Application Priority Data

Feb. 17, 1995 [JP] Japan ..................................... 7-029763

[51] Int. Cl.$^6$ ....................... C07D 209/08; C07D 403/06
[52] U.S. Cl. ........................ 548/465; 548/490; 548/491; 548/510
[58] Field of Search .................... 548/465, 510, 548/491, 490

[56] References Cited

U.S. PATENT DOCUMENTS

| | | | |
|---|---|---|---|
| 3,702,323 | 11/1972 | Yamamoto et al. ................. | 260/239.3 |
| 5,538,991 | 7/1996 | Ashton et al. ........................... | 514/397 |
| 5,677,326 | 10/1997 | Tsuchiya et al. ....................... | 514/394 |

FOREIGN PATENT DOCUMENTS

| | | |
|---|---|---|
| 0 287 196 | 10/1988 | European Pat. Off. . |
| A-52-12162 | 1/1977 | Japan . |
| PCT/JP94/ 01641 | 9/1994 | Japan . |
| WO 95/09167 | 4/1995 | Japan . |
| 1 550 230 | 8/1979 | United Kingdom . |

*Primary Examiner*—Joseph K. McKane
*Attorney, Agent, or Firm*—McGlew & Tuttle, P.C.

[57] ABSTRACT

This invention concerns a method for the production of a 3-arylindoline compound represented by the general formula

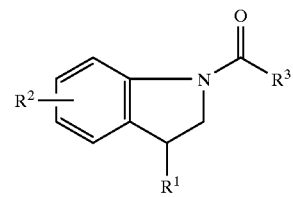

25 Claims, No Drawings

PROCESS FOR PRODUCING INDOLINE COMPOUNDS AND INTERMEDIATES FOR THE PRODUCTION OF THE SAME

This application is a 371 of PCT/JP96/00344 filed Feb. 16, 1996.

TECHNICAL FIELD

This invention relates to a method for the production of a 3-(hetero)arylindoline compound (hereinafter referred to simply as "3-arylindoline compound") useful for the production of 1-acyl-3-(hetero)arylindoline compound, the 5-$HT_3$ receptor antagonist, (hereinafter referred to simply as "1-acyl-3-arylindoline compound"), 1-acyl-3-(hetero)arylindole compound, an intermediate for the production thereof, (hereinafter referred to simply as "1-acyl-3-arylindole compound"), and a method for the production of an optically active 1-acyl-3-arylindoline compound.

BACKGROUND ART

A 1-acyl-3-arylindoline compound represented by the general formula (1)

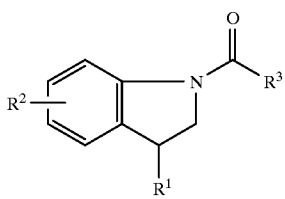

(wherein $R^1$ represents an optionally substituted phenyl group or an aromatic heterocyclic group, $R^2$ represents a hydrogen atom, a halogen atom, a lower alkyl group, a hydroxy group, a lower alkoxy group, a carbamoyl group, or a lower alkoxycarbonyl group, and $R^3$ represents a group of the following formula)

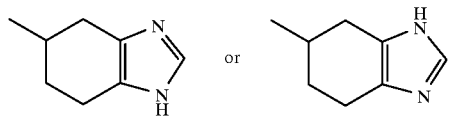

is a compound useful as the 5-$HT_3$ receptor antagonist (PCT/JP94/01641), and is produced by the condensation reaction of a 3-arylindoline compound represented by the general formula (2)

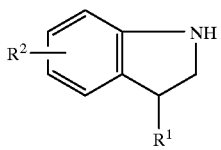

(wherein $R^1$ and $R^2$ have the same meanings as defined above) with a carboxylic acid compound represented by the general formula (3)

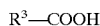

$R^3$—COOH (wherein $R^3$ has the same meaning as defined above) or a reactive derivative thereof.

As means to produce the 3-arylindoline compound (2), methods for reducing a 3-arylindole compound represented by the general formula (4)

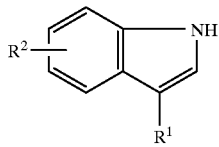

(wherein $R^1$ and $R^2$ have the same meanings as defined above) under strongly acidic conditions, namely a method for effecting the reduction catalytically in the presence of such an strongly electrophilic reagent as a mineral acid like hydrochloric acid, hydrofluobromic acid, or orthophosphoric acid or an organic acid (preferably glacial acetic acid, propionic acid, trifluoroacetic acid, or formic acid) in the presence of such a Lewis acid as boron trifluoride, aluminum trichloride, or zinc chloride and a strongly acidic chemical reduction system for effecting the reduction by the use of boron trifluoride/zinc dust/glacial acetic acid or zinc dust/hydrochloric acid, have been known (JP-A-52-12,162). These methods, however, are invariably unfit for the reduction of an indole compound which is unstable under acidic conditions and are barely capable of producing a 3-arylindoline compound in a yield in the neighborhood of 50%. Further, since the reactions used by the methods are carried out under strongly acidic conditions, they are liable to corrode pressure reaction vessels made of a metal, by-produce copiously a toxic zinc compound, and incur difficulty in enabling the reaction product to be refined by the separation of the zinc compound. These factors render infeasible the commercialization of these methods.

As concrete examples of the means to produce an optically active substance of a 1-acyl-3-arylindoline compound (1), a method which comprises condensing an optically active substance of a 3-arylindoline compound (2) with an optically active substance of a carboxylic acid compound (3), a method which comprises separating by column chromatography an epimer mixture obtained by the condensation of a 3-arylindoline compound (2) and a carboxylic acid compound (3), either of them is an optically active substance and the remainder a racemic substance, and a method which comprises condensing a 3-arylindoline compound (2) and a carboxylic acid compound (3), both of which are racemic substances, thereby forming a diastereomer mixture, separating this mixture by column chromatography, and then optically resolving the components as by means of fractional recrystallization may be cited. A need is felt for a method of production which has as few component steps as possible, excels in operational efficiency, and permits production in a high yield.

DISCLOSURE OF THE INVENTION

This invention has been produced in view of the problematic points mentioned above regarding the method for the production of a 1-acyl-3-arylindoline compound (1), the 5-$HT_3$ receptor antagonist. An object of this invention, therefore, is to provide a novel method for the production of a 3-arylindoline compound (2) which is used for a 1-acyl-3-arylindoline compound (1). A further object of this invention is to provide a novel method for the production of the optically active substance of a 3-arylindoline compound (2) which is used for the production of an optically active 1-acyl-3-arylindoline compound (1) and an intermediate for the production thereof. Another object of this invention is to provide a method for the production of the optically active substance of a 1-acyl-3-arylindoline compound (1).

The present inventors, after continuing a diligent study with a view to attaining the objects mentioned above, have found that a 1-acyl-3-arylindole compound obtained by having a removable electron withdrawing group linked thereto by acylating the 1 position of a 3-arylindole compound with such an organic acid as carboxylic acid or sulfonic acid easily undergoes a catalytic reduction under neutral or weakly acidic conditions and gives rise to a 1-acyl-3-arylindoline compound and that an optically active 1-acyl-3-arylindole compound obtained by the acylation with an organic acid such as optically active carboxylic acid or sulfonic acid produces an optically active 1-acyl-3-arylindoline compound with high selectivity by the reaction of a catalytic reduction. They have perfected this invention as a result.

By this invention is provided a method for the production of a 3-arylindoline compound (2) which is used for the production of a 1-acyl-3-arylindoline compound, the 5-$HT_3$ receptor antagonist.

Specifically, the 3-arylindoline compound (2) can be obtained by subjecting a 1-acyl-3-arylindole compound represented by the general formula (6)

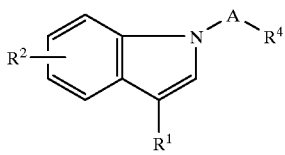

(wherein $R^1$, $R^2$, have the same meanings as defined above, $R^4$ represents an optionally substituted linear, branched, or cyclic alkyl group, aryl group, or an aromatic or saturated heterocyclic group, and A represents a carbonyl group or sulfonyl group) which can be produced by condensing a 3-arylindole compound (4) with an organic acid such as carboxylic acid or sulfonic acid represented by the general formula (5)

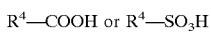

$R^4$—COOH or $R^4$—$SO_3H$ (wherein $R^4$ has the same meaning as defined above) or a reactive derivative thereof to a reduction reaction thereby obtaining a 1-acyl-3-arylindoline compound represented by the general formula (7)

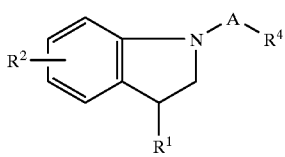

(wherein $R^1$, $R^2$, $R^4$, and A have the same meanings as defined above) and hydrolyzing this 1-acyl-3-arylindoline compound.

As concrete examples of $R^1$ as an aromatic heterocyclic group, the monovalent groups which can be derived from thiophene, oxazole, thiazole, furan, pyran, pyrrole, imidazole, pyrazole, isothiazole, isoxazole, pyridine, pyrazine, pyrimidine, pyridazine, indole, quinoline, and isoquinoline may be cited. As concrete examples of the substituent for $R^1$, lower alkyl groups such as methyl, ethyl, propyl, and isopropyl, hydroxy group, lower alkoxy groups such as methoxy, ethoxy, propoxy, and isopropyloxy, halogen atoms such as fluorine, chlorine, and bromine, amino group, lower alkyl amino groups such as methyl amino and dimethyl amino, alkyl carbamoyl group, carbamoyl group, sulfamoyl group, lower alkoxy carbonyl groups such as methoxy carbonyl, nitro group, and acyl amino groups such as acetyl amino and propionyl amino may be cited.

As concrete examples of $R^2$, hydrogen atom, halogen atoms such as fluorine, chlorine, and bromine, lower alkyl groups such as methyl, ethyl, propyl, and isopropyl, hydroxy group, lower alkoxy groups such as methoxy, ethoxy, propoxy, and isopropyloxy, carbamoyl group, and lower alkoxycarbonyl groups such as methoxy carbonyl may be cited.

As concrete examples of $R^4$, the monovalent groups which can be derived from linear alkyl groups such as methyl, ethyl, and propyl, branched alkyl groups such as isopropyl and isobutyl, cyclic alkyl groups such as cyclohexyl, aryl groups such as phenyl, 3-chlorophenyl, 4-methyl phenyl, 2-methoxy phenyl, 4-carbamoyl phenyl, 3-methoxy carbonyl phenyl, and naphthyl, and aromatic heterocycles such as thiophene, oxazole, thiazole, furan, pyrane, pyrrole, imidazole, pyrazole, isothiazole, isooxazole, pyridine, pyrazine, pyrimidine, pyridazine, indole, quinoline, and isoquinoline and the monovalent groups which can be derived from saturated heterocycles such as tetrahydrofuran, tetrahydropyrane, pyrrolidine, imidazolidine, pyrazolidine, piperidine, piperazine, quinuclidine, and morpholine. As concrete examples of the substituent which is optionally possessed by these groups, halogen atoms such as fluorine, chlorine, and bromine, amino group which is optionally protected by urethane type protective groups such as benzyloxycarbonyl, p-methoxybenzyloxycarbonyl, p-chlorobenzyloxycarbonyl, p-nitrobenzyloxycarbonyl, 3,5-dimethoxybenzyloxycarbonyl, tertiarybutyloxycarbonyl, tertiaryamyloxycarbonyl, p-biphenylisopropyloxycarbonyl, diisopropylmethyloxycarbonyl, or fulfuryloxy carbonyl, acyl type protective groups such as formyl, trifluoroacetyl, tosyl, o-nitrophenylsulfenyl, p-methoxy-o-nitrophenylsulfenyl, benzoyl, chloroacetyl, or acetoacetyl, or alkyl group protective groups such as trytyl, benzylidene, benzyl, 2-benzoyl-1-methylvinyl, or trimethylsilyl, lower alkylamino groups such as methyl amino and dimethyl amino, alkylcarbamoyl groups, carbamoyl group, sulfamoyl group, lower alkoxycarbonyl groups such as methoxycarbonyl, and lower alkyl groups such as methyl, ethyl, propyl, and isopropyl, hydroxy group which is optionally protected by benzyl, acetyl, trifluoroacetyl, or benzyloxy carbonyl, lower alkoxy groups such as methoxy, ethoxy, propoxy, and isopropyloxy, and acyl groups such as acetyl and propionyl, and mercapto group which is optionally protected by benzyl, p-methoxybenzyl, or trytyl, lower alkylthio groups such as methylthio group, sulfinyl groups such as methylsulfinyl and phenylsulfinyl, sulfonyl groups such as methylsulfonyl, benzenesulfonyl, and p-toluenesulfonyl, and aryl groups such as phenyl, 3-chlorophenyl, 4-methylphenyl, 2-methoxyphenyl, 4-carbamoylphenyl, 3-methoxycarbonylphenyl, and naphthyl may be cited. When an amino group is present in the saturated heterocycle, this amino group may be protected by the protective group of the amino group mentioned above.

As concrete examples of the organic acid (5), acetic acid, propionic acid, butyric acid, mandelic acid, camphocarboxylic acid, malic acid, tartaric acid, cyclohexanecarboxylic acid, benzoic acid, toluic acid, fluorobenzoic acid, chlorobenzoic acid, methoxybenzoic acid, carbamoylbenzoic acid, methoxycarbonylbenzoic acid, naphthoic acid, furancarboxylic acid, thiophenecarboxylic acid, and pyridinecarboxylic acid, amino acids such as alanine, valine, phenylalanine, leucine, isoleucine, methionine, glutamine, asparagine, and proline which are protected by the protective group of the amino group mentioned above, p-toluenesulfonic acid, and camphorsulfonic acid, e.g. 10-camphorsulfonic acid, may be cited.

As concrete examples of the 1-acyl-3-arylindole compound (6), 1-benzoyl-3-phenylindole, 1-acetyl-3-phenylindole, 1-benzoyl-3-(3-methoxyphenyl)indole, 1-trifluoroacetyl-3-phenylindole, 1-cyclohexylcarbonyl-3-phenylindole, 3-(4-fluorophenyl)-1-(4-methylphenylcarbonyl)indole, 1-(1-naphthylcarbonyl)-3-phenylindole, 5-fluoro-3-(2-methoxyphenyl)-1-(3-pyridylcarbonyl)indole, 1-benzoyl-6-methoxycarbonyl-3-(4-methoxyphenyl)indole, 3-phenyl-1-(N-tosylprolyl)indole, and 3-(3-methoxyphenyl)-1-(N-tosylprolyl)indole may be cited.

As concrete examples of the 1-acyl-3-arylindoline compound (7), 1-benzoyl-3-phenylindoline, 1-acetyl-3-phenylindoline, 1-benzoyl-3-(3-methoxyphenyl)indoline, 1-trifluoroacetyl-3-phenylindoline, 1-cyclohexylcarbonyl-3-phenylindoline, 3-(4-fluorophenyl)-1-(4-methylphenylcarbonyl)indoline, 1-(1-naphthylcarbonyl)-3-phenylindoline, 5-fluoro-3-(2-methoxyphenyl)-1-(3-pyridyl carbonyl)indoline, 1-benzoyl-6-methoxycarbonyl-3-(4-methoxyphenyl)indoline, 3-phenyl-1-(N-tosylprolyl)indoline, and 3-(3-methoxyphenyl)-1-(N-tosylpropyl)indoline may be cited.

The method for producing the 3-arylindoline compound (2) of this invention will be described more specifically below. First, the 1-acyl-3-arylindole compound (6) is obtained by subjecting the 3-arylindole compound (4) and the organic acid (5) or a reactive derivative thereof to a condensation reaction. The reaction solvent has only to avoid participating in the reaction. An ether type solvent such as tetrahydrofuran may be cited as a concrete example. When the organic acid is used in its unmodified form in the reaction, this reaction is carried out in the presence of a standard condensing agent to be used in the reaction for the formation of an amide bond. N,N'-dicyclohexylcarbodiimide may be cited as a concrete example of the condensing agent. The reactive derivatives of the organic acid may be those which are generally used in the reaction for the formation of an amide bond. Acid halides and acid anhydrides may be cited as concrete examples. The reaction is carried out in the presence or absence of a base at normal room temperature or in a heated or cooled state, preferably at a temperature in the range of from −80° C. to 100° C.

Next, the 1-acyl-3-arylindoline compound (7) is obtained by reducing the 1-acyl-3-arylindole compound (6) by the catalytic hydrogenation reaction which is popularly adopted. The reaction solvent has only to avoid participating in the reaction. Ethanol and acetic acid may be cited as concrete examples of the reaction solvent. A palladium catalyst may be cited as a concrete example of the catalyst for the reaction. The reaction is carried out under normal pressure or under an increased pressure, at normal room temperature or in a heated or cooled state, preferably at a temperature in the range of from 0° C. to 100° C.

When the 1-acyl-3-arylindoline compound (7) consequently obtained is hydrolyzed in the presence of an acid or a base, it can be easily converted into the 3-arylindoline compound (2).

The 3-arylindoline compound (2) is easily colored and decomposed at normal room temperature and is not fit to be conserved as an intermediate for the production of the 1-acyl-3-arylindoline compound (1). In contrast, the 1-acyl-3-arylindole compound (6) and the 1-acyl-3-arylindoline compound (7) are stable at normal room temperature and fit for storage in bulk and perfectly excellent as an intermediate for the production of the 1-acyl-3-arylindoline compound (1).

By the present invention are provided a method for the production of an optically active 3-arylindoline compound represented by the general formula (8)

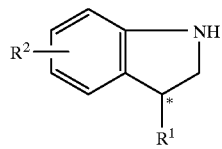

(wherein $R^1$ and $R^2$ have the same meanings as defined above and * indicates the asymmetric center of an optically active compound), which is an optically active substance of the 3-arylindoline compound (2) and an intermediate for the production thereof. To be specific, in the method for the production of the 3-arylindoline compound (2) mentioned above, an optically active 1-acyl-3-arylindoline compound represented by the general formula (11)

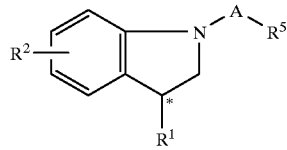

(wherein $R^1$, $R^2$, A, and * have the same meanings as defined above and $R^5$ represents an optionally substituted linear, branched, or cyclic alkyl group, aryl group, or aromatic or saturated heterocyclic group possessed of asymmetry) can be selectively obtained by the asymmetric reduction of an optically active 1-acyl-3-arylindole compound represented by the general formula (10)

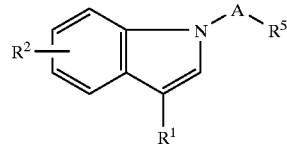

(wherein $R^1$, $R^2$, $R^5$, and A have the same meanings as defined above) which is obtained by using the 3-arylindole compound (4) and an optically active organic acid represented by the general formula (9)

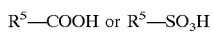

$R^5$—COOH or $R^5$—SO$_3$H (wherein $R^5$ has the same meaning as defined above).

As concrete examples of the optically active organic acid, optically active mandelic acid, camphocarboxylic acid, malic acid, and tartaric acid which are generally used for optical resolution, amino acids such as alanine, valine, phenyl alanine, leucine, isoleucine, glutamine, asparagine, and proline which protect amino groups, and 10-camphorsulfonic acid may be cited. Among other optically active organic acids mentioned above, D-proline derivatives and L-proline derivatives which are represented by the general formula (12) prove particularly advantageous.

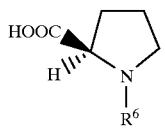

R$^6$ has to be a protective group for those amino groups which are generally used in the synthesis of peptides. As concrete examples of the protective group, urethane type protective groups such as benzyloxycarbonyl, p-methoxybenzyloxycarbonyl, p-chlorobenzyloxycarbonyl, p-nitrobenzyloxycarbonyl, 3,5-dimethoxybenzyloxycarbonyl, tert-butyloxycarbonyl, tert-amyloxycarbonyl, p-biphenylisopropyloxycarbonyl, diisopropylmethyloxycarbonyl, or fulfuryloxycarbonyl, acyl type protective groups such as formyl, trifluoroacetyl, tosyl, o-nitrophenylsulfenyl, p-methoxy-o-nitrophenylsulfenyl, benzoyl, chloroacetyl, or acetoacetyl, or alkyl group protective groups such as trytyl, benzylidene, benzyl, 2-benzoyl-1-methylvinyl, or trimethylsilyl may be preferably cited.

As preferred examples of the optically active 1-acyl-3-arylindole compound (10), 1-D-prolyl-3-arylindole compounds represented by the general formula (13)

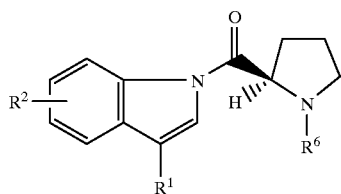

(wherein R$^1$, R$^2$, and R$^6$ have the same meanings as defined above) may be cited. As particularly preferred examples thereof, 1-(N-benzyloxycarbonyl-D-prolyl)-3-phenylindole, 3-phenyl-1-(N-tosyl-D-prolyl)indole, 3-phenyl-1-(N-trifluoroacetyl-D-prolyl)indole, 1-(N-trytyl-D-prolyl)-3-phenylindole, 3-(3-hydroxyphenyl)-1-(N-tosyl-D-prolyl) indole and 3-(3-methoxyphenyl)-1-(N-tosyl-D-prolyl)indole may be cited.

As preferred examples of the optically active 1-acyl-3-arylindoline compound (11), 1-D-prolyl-3-arylindoline compounds represented by the general formula (14)

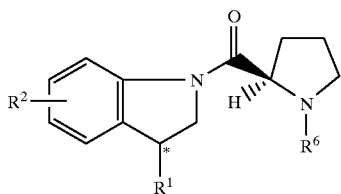

(wherein R$^1$, R$^2$, R$^6$, and * have the same meanings as defined above) may be cited. As particularly preferred examples thereof, 1-(N-benzyloxycarbonyl-D-prolyl)-3-phenylindoline, 3-phenyl-1-(N-tosyl-D-prolyl)indoline, 3-phenyl-1-(N-trifluoroacetyl-D-prolyl)indoline, 1-(N-trytyl-D-prolyl)-3-phenylindoline, 3-(3-hydroxyphenyl)-1-(N-tosyl-D-prolyl)indoline and 3-(3-methoxyphenyl)-1-(N-tosyl-D-prolyl)indoline may be cited. The production of the optically active 3-arylindoline compound (8) from the optically active 1-acyl-3-arylindoline compound (11) obtained as described above can be accomplished by the hydrolysis which is performed under the standard condition for the removal of the protective group of the amino group.

By this invention is provided a method for the production of an optically active 1-acyl-3-arylindoline compound represented by the general formula (15)

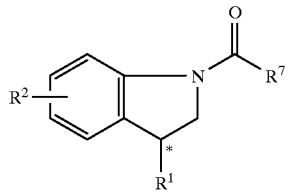

[wherein R$^1$, R$^2$, and * have the same meanings as defined above and R$^7$ represents the following group

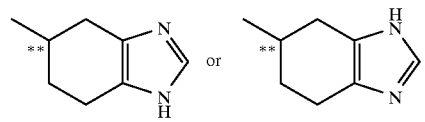

(wherein ** indicates the asymmetric center of an optically active compound, independently of *)], which is the optically active substance of the 1-acyl-3-arylindoline compound (1), i.e. the 5-HT$_3$ receptor antagonist.

Specifically, the optically active 1-acyl-3-arylindoline compound (11) can be produced by reducing the optically active 1-acyl-3-arylindole compound (10) obtained by condensing the 3-arylindole compound (4) with the optically active organic acid (9), then hydrolyzing this compound (11) into the optically active 3-arylindoline compound (8), condensing this compound (8) with the carboxylic acid compound (3) as a racemic substance thereby forming an epimer mixture of a 1-acyl-3-arylindoline compound represented by the general formula (16)

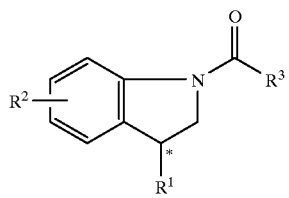

(wherein R$^1$, R$^2$, R$^3$, and * have the same meanings as defined above), and the optically active 1-acyl-3-arylindoline compound (15) can be produced by fractionally recrystallizing this epimer mixture.

The optically active 1-acyl-3-arylindoline compound can be obtained as expected by suitably selecting the recrystallizing solvent or by repeating the recrystallization. As the recrystallizing solvent, one single solvent or a mixture of a plurality of solvents may be used. As preferred examples of the recrystallizing solvent, alcohols such as methanol, ethanol, and isopropylalcohol and lower fatty esters such as ethyl acetate may be cited.

BEST MODE FOR EMBODYING THE INVENTION

Now, this invention will be described more specifically below with reference to working examples.

REFERENTIAL EXAMPLE 1

Hydrochloride of 4,5,6,7-tetrahydrobenzimidazole-5-carboxylic acid

A mixture of 10.0 g of sulfate of benzimidazole-5-carboxylic ethyl ester, 5.0 g of 5% palladium-carbon catalyst, and 100 ml of ethanol was stirred in hydrogen for five hours under the conditions of 135° C. and 50 kg/cm², cooled, then filtered to separate the catalyst, and distilled to expel the ethanol. The residue of the distillation was neutralized with an aqueous sodium bicarbonate solution and extracted with chloroform. The chloroform layer was dried over anhydrous magnesium sulfate and then distilled to expel chloroform and obtain 6.9 g of 4,5,6,7-tetrahydrobenzimidazole-5-carboxylic ethyl ester. This ester and 200 ml of 6N hydrochloric acid added thereto were refluxed together for seven hours. The hydrochloric acid solution was concentrated to dryness, crystallized by addition of acetone, separated by filtration, and then dried to obtain 6.9 g of hydrochloride of 4,5,6,7-tetrahydrobenzimidazole-5-carboxylic acid.

REFERENTIAL EXAMPLE 2

Sulfate of 4,5,6,7-tetrahydrobenzimidazole-5-carboxylic acid

A mixture of 2.0 g of benzimidazole-5-carboxylic acid, 2.5 g of 5% palladium-carbon catalyst, 30 ml of acetic acid, and 0.65 ml of sulfuric acid was stirred in hydrogen for six hours under the conditions of 105° C. and 50 kg/cm², cooled, filtered to remove the catalyst, and distilled to expel the acetic acid. The residue of the distillation was crystallized by addition of acetone, separated by filtration, and dried to obtain 2.4 g of sulfate of 4,5,6,7-tetrahydrobenzimidazole-5-carboxylic acid.

$^1$H-NMR ($\delta$ ppm, D20, 270 MHz): 1.9–2.1 (1H, m), 2.1–2.3 (1H, m), 2,6–3.1 (5H, m), 8.47 (1H, s)

REFERENTIAL EXAMPLE 3

Optically active 5-(3-phenylindolin-1-ylcarbonyl- 4,5,6,7-tetrahydrobenzimidazole A white powder containing 11 g of hydrochloride of (+)-4,5,6,7-tetrahydrobenzimidazole-5-carboxylic acid was mixed with 80 ml of thionyl chloride and the produced mixture was refluxed for two hours. The reaction solution was concentrated under a reduced pressure and the resultant residue was solved in 200 ml of chloroform. A solution of 7.9 g of (+)-3-phenylindoline in 50 ml of chloroform was added as cooled with ice to the chloroform solution mentioned above. Then, to the resultant reaction solution, a solution of 8.2 ml of triethyl amine in 20 ml of chloroform was added dropwise over a period of two hours. The reaction solution was allowed to warm to room temperature, stirred for two hours, made to add a saturated aqueous sodium bicarbonate solution, extracted with chloroform, dried, and concentrated to obtain a white residue. The residue was crystallized by addition of ethyl acetate and the crystal was separated by filtration and recrystallized twice from a mixed solvent of chloroform and ethyl acetate to obtain 12 g of an optically active 5-(3-phenylindolin-1-ylcarbonyl)-4,5,6,7-tetrahydrobenzimidazole (yield 86.4%).

$^1$H-NMR ($\delta$ ppm, CDC 13, 270 MHz): 1.9–2.2 (2H, m), 2,5–3.2 (5H, m), 4.0–4.1 (1H, m), 4.5–4.7 (2H, m), 6.9–7.1 (2H, m), 7.1–7.4 (6H, m), 7.53 (1H, 3), 8.34 (1H, d)

HPLC (Column; CAPCELL PAK C18 SG120, 4.6 mm in Diam.×150 mm, eluting solvent; 50 mM (NH$_4$)$_2$HPO$_4$:MeOH=1:1, flow rate; 0.8 ml/minute, temperature; 35° C.): retention time 35.70 minutes HPLC (Column; CHIRALCEL OD, 4.6 mm in Diam.×50 mm Produced by Daicel Kagaku Kogyo K.K., eluting solvent; n-hexane; isopropylalcohol=6:1, flow rate; 0.8 ml/minute); retention time 19.24 minutes

EXAMPLE 1

1-Benzoyl-3-phenyl indole

In 400 ml of tetrahydrofuran, 42.0 g of 3-phenyl indole was solved. The solution and 25.0 g of potassium tert-butoxide added thereto at −30−−20° C. were together heated to normal room temperature and stirred for 30 minutes. The reaction solution was cooled to −20−−10° C. and 26 ml of benzoyl chloride added thereto were together heated to normal room temperature and stirred for one hour. The resultant mixture was poured into ice water and extracted with chloroform. The chloroform layer was dried over anhydrous magnesium sulfate, distilled to expel the chloroform, crystallized by addition of isopropyl ether, separated by filtration, and dried to obtain 60.0 g of 1-benzoyl-3-phenylindole (92.8%) having a melting point of 154–156° C.

$^1$H-NMR ($\delta$ ppm, DMSO-d6, 270 MHz): 7.3–7.55 (5H, m), 7.55–7.8 (6H, m), 7.84 (2H, m), 7.90 (1H, m), 8.37 (1H, m)

EXAMPLE 2

1-Acetyl-3-phenylindole

From 4.0 g of 3-phenylindole, 3.8 g of 1-acetyl-3-phenylindole (78.0%) having a melting point of 136–1380C. was obtained by following the procedure of Example 1 substantially faithfully while using acetyl chloride in the place of benzoyl chloride.

$^1$H-NM ($\delta$ PPM, CDC13, 270 MHz): 2.68 (3H, 3), 7.30–7.55 (6H, m), 7.60–7.68 (2H, m), 7.77–7.83 (1H, m), 8.52 (1H, d)

EXAMPLE 3

1-Benzoyl-3-(3-methoxyphenyl)indole

By following the procedure of Example 1 faithfully while using 45.0 g of 3-(3-methoxyphenyl)indole in the place of 3-phenylindole, 42.9 g of 1-benzoyl-3-(3-methoxyphenyl)indole (65.0%) was obtained.

1H-NMR ($\delta$ ppm, CDC 13, 270 MHz): 3.85 (3H, 3), 6.87–6.94 (1H, m), 7.10–7.25 (2H, m), 7.30–7.67 (7H, m), 7.75–7.82 (2H, m), 7.85–7.90 (1H, m), 8.47 (1H, d)

EXAMPLE 4

5-Fluoro-3-(2-methoxyphenyl)-1-nicotinoylindole

By following the procedure of Example 1 substantially faithfully while using 10.0 g of 5-fluoro-3-(2-methoxyphenyl)indole in the place of 3-phenylindole and using nicotinoyl chloride in the place of benzoyl chloride, 9.5 g of 5-fluoro-3-(2-methoxyphenyl)-1-nicotinoylindole (66.0%) was obtained.

EXAMPLE 5

1-Benzoyl-6-methoxycarbonyl-3-(4-methoxyphenyl) indole

By following the procedure of Example 1 substantially faithfully while using 10.0 g of 6-methoxycarbonyl-3-(4-methoxyphenyl)indole in the place of 3-phenylindole, 8.2 g of 1-benzoyl-6-methoxycarbonyl-3-(4-methoxyphenyl) indole (59.9%) was obtained.

EXAMPLE 6

1-Benzoyl-3-phenylindoline

A mixture of 3.0 g of 1-benzoyl-3-phenylindole, 0.33 g of 10% palladium-carbon catalyst, and 60 ml of acetic acid was stirred in hydrogen for six hours under the conditions of 60° C. and normal pressure, cooled, then filtered to remove the catalyst, and distilled to expel the acetic acid. The residue was alkalinized by addition of an aqueous sodium hydroxide solution and extracted with ethyl acetate. The ethyl acetate layer was dried over anhydrous magnesium sulfate, and then distilled to expel the ethyl acetate and obtain 2.94 g of 1-benzoyl-3-phenylindoline (97.4%) having a melting point of 127–129° C.

$^1$H-NMR ($\delta$ ppm, CDC13, 270 MHz): 3.90–4.10 (1H, m), 4.35–4.55 (1H, m), 4.56 (1H, t), 6.98–7.60 (14H, m)

EXAMPLE 7

1-Benzoyl-3-phenylindoline

By following the procedure of Example 6 substantially faithfully while using ethanol in the place of the acetic acid and using a pressure of 5–6.4 kg/cm$^2$ in the place of normal pressure, 12.0 g of 1-benzoyl-3-phenylindoline (99.3%) was obtained from 12.0 g of 1-benzoyl-3-phenylindole.

EXAMPLE 8

1-Acetyl-3-phenylindoline

By following the procedure of Example 6 substantially faithfully, 1.01 g of 1-acetyl-3-phenylindoline (100%) was obtained from 1.00 g of 1-acetyl-3-phenylindole.

$^1$H-NMR ($\delta$ ppm, CDC13, 270 MHz): 2.22 (3H, s), 3.95 (1H, dd), 4.46 (1H, t), 4.63 (1H, dd), 6.95–7.05 (2H, m), 7.15–7.40 (6H, m), 8.28 (1H, d)

EXAMPLE 9

3-Phenylindoline

The amount, 5.50 g, of the 1-benzoyl-3-phenylindoline obtained in Example 6 and a solution of 4.0 g of sodium hydroxide in 40 ml of water and 84 ml of ethanol added thereto were refluxed together for six hours. The reaction solution was poured into ice water and extracted with ethyl acetate. The ethyl acetate layer was washed with an aqueous potassium carbonate solution, then dried over anhydrous magnesium sulfate, and distilled to expel the ethyl acetate and obtain 3.49 g of 3-phenylindoline (97.2%) in the form of an oily semi-solid substance.

$^1$H-NMR ($\delta$ ppm, CDC13, 270 MHz): 3.5 (1H, brs), 3.50 (1H, t), 3.93 (1H, t), 4.49 (1H, t), 6.6–6.8 (2H, m), 6.91 (1H, d), 7.07 (1H, t), 7.2–7.4 (5H, m)

EXAMPLE 10

3-Phenylindoline

By following the procedure of Example 9 faithfully while using 1.0 g of the 1-acetyl-3-phenylindoline obtained in Example 8 in the place of 1-benzoyl-3-phenylindoline, 0.82 g of 3-phenylindoline (99.8%) was obtained.

EXAMPLE 11

1-Benzoyl-3-(3-methoxyphenyl)indoline

By following the procedure of Example 6 faithfully while using 3.00 g of 1-benzoyl-3-(3-methoxyphenyl)indole in the place of 1-benzoyl-3-phenylindole, 2.75 g of 1-benzoyl-3-(3-methoxyphenyl)indoline (91.1%) was obtained.

$^1$H-NMR ($\delta$ ppm, CDC13, 270 MHz): 3.76 (3H, s), 3.95–4.10 (1H, m), 4.35–4.55 (1H, m), 4.53 (1H, t), 6.70–6.84 (3H, m), 6.95–7.05 (2H, m), 7.20–7.30 (2H, m), 7.35–7.60 (6H, m)

EXAMPLE 12

3-(3-Methoxyphenyl)indoline

By following the procedure of Example 9 faithfully while using 1.00 g of 1-benzoyl-3-(3-methoxyphenyl)indoline in the place of 1-benzoyl-3-phenylindoline, 0.66 g of 3-(3-methoxyphenyl)indoline (96.5%) was obtained in the form of an oily semi-solid substance.

$^1$H-NMR ($\delta$ ppm, CDC13, 270 MHz): 3.50 (1H, t), 3.8 (1H, br), 3.78 (3H, s), 3.93 (1H, t), 4.46 (1H, t), 6.6–7.0 (6H, m) 7.07 (1H, t), 7.2–7.3 (1H, m)

EXAMPLE 13

5-Fluoro-3-(2-methoxyphenyl)indoline

By following the procedure of Example 6 substantially faithfully while using 3.0 g of 5-fluoro-3-(2-methoxyphenyl)-1-nicotinoylindole in the place of 1-benzoyl-3-phenylindole, 2.7 g of 5-fluoro-3-(2-methoxyphenyl)-1-nicotinoylindoline (89.4%) was obtained. By further subjecting this compound to the same reaction as used in the procedure of Example 9, 1.2 g of 5-fluoro-3-(2-methoxyphenyl)indoline (63.5%) was obtained.

EXAMPLE 14

6-Methoxycarbonyl-3-(4-methoxyphenyl)indoline

By following the procedure of Example 6 substantially faithfully while using 3.0 g of 1-benzoyl-6-methoxycarbonyl-3-(4-methoxyphenyl)indole in the place of 1-benzoyl-3-phenylindole, 1-benzoyl-6-methoxycarbonyl-3-(4-methoxyphenyl)indoline was obtained. This compound was subjected to the same reaction as used in the procedure of Example 9 and then refluxed in a mixture of thionyl chloride and methanol. The resultant reaction product was refined by silica gel column chromatography to obtain 0.7 g of 6-methoxycarbonyl-3-(4-methoxyphenyl)indoline (31.7%).

EXAMPLE 15

3-Phenyl-1-(N-tosyl-D-prolyl)indole

By following the procedure of Example 1 substantially faithfully while using N-tosyl-D-prolyl chloride in the place of benzoyl chloride and changing the reaction temperature during the course of cooling to –40° C., 3.88 g of 3-phenyl-1-(N-tosyl-D-prolyl)indole (48.2%) having a melting point of 148–149° C. was obtained from 3.50 g of 3-phenylindole.

$^1$H-NMR ($\delta$ ppm, CDC13, 270 MHz): 1.90–2.50 (4H, m), 2.40 (3H, s), 3.50–3.70 (2H, m), 5.28 (1H, dd), 7.25–7.55 (7H, m), 7.63–7.70 (3H, m), 7.75–7.85 (3H, m), 8.47 (1H, dd)

EXAMPLE 16

(+)-3-Phenylindoline

By following the procedure of Example 6 substantially faithfully while using 2.00 g of 3-phenyl-1-(N-tosyl-D-prolyl) indole in the place of 1-benzoyl-3-phenyl indole, 1.81 g of 3-phenyl-1-(N-tosyl-D-prolyl)indoline (90.0%) was obtained. This compound and 4.7 ml of concentrated hydrochloric acid and 12.4 ml of acetic acid added thereto were together refluxed for 37 hours. The product of reflux was weakly alkalinized with an aqueous sodium hydroxide solution and extracted with ethyl acetate. The ethyl acetate layer was dried over anhydrous magnesium sulfate and then distilled to expel the ethyl acetate. The residue of the distillation was refined by silica gel column chromatography to obtain 0.77 g of (+)-3-phenylindoline (97.5%). The $^1$H-NMR of this product coincided with that shown in Example 9.

HPLC (Column; CHIRALCEL OD, 4.6 mm in Diam.× 250 mm, produced by Daicel Kagaku Kogyo K.K., eluting solvent; n-hexane:ethanol=4:1, flow rate; 1 ml/minute, column temperature 40° C.; detection wavelength 250 nm); retention time 5.53 minutes

[α] D=+51.0° (c=0.10, MeOH)

EXAMPLE 17

3-Phenyl-1-(N-trifluoroacetyl-D-prolyl)indole

By following the procedure of Example 1 substantially faithfully while using N-trifluoroacetyl-D-prolyl chloride in the place of benzoyl chloride and changing the reaction temperature during the course of cooling to −40° C., 2.29 g of 3-phenyl-1-(N-trifluoroacetyl-D-prolyl)indole (28.6%) was obtained from 4.00 g of 3-phenylindole.

$^1$H-NMR (δ ppm, CDC13, 270 MHz): 2.00–2.55 (4H, m), 3.70–4.05 (2H, m), 5.40 (1H, dd), 7.32–7.57 (6H, m), 7.60–7.67 (2H, m), 7.77–7.83 (1H, m), 8.51 (1H, d)

EXAMPLE 18

(+)-3-Phenylindoline

By following the procedure of Example 6 substantially faithfully while using 5.00 g of 3-phenyl-1-(N-trifluoroacetyl-D-prolyl)indole in the place of 1-benzoyl-3-phenylindole, 4.91 g of 3-phenyl-1-(N-trifluoroacetyl-D-prolyl)indoline (97.6%) was obtained. By subjecting this compound to the same procedure as in Example 16, 2.39 g of (+)-3-phenylindoline (96.8%) was obtained.

The $^1$H-NMR of this product coincided with that shown in Example 9.

[α] D=+17.4° (c=0.10, MeOH)
Optical purity: 33.4% e.e.

EXAMPLE 19

5-(3-Phenylindolin-1-ylcarbonyl)-4,5,6,7-tetrahydrobenzimidazole

A mixed solution of 518 mg of hydrochloride (racemic form) of 4,5,6,7-tetrahydrobenzimidazole-5-carboxylic acid, 500mg of (+)-3-phenylindoline, and 15 ml of dimethyl formamide was cooled to 0° C. The cooled solution and 736 mg of hydrochloride of N-ethyl-N'-(3-dimethylaminopropyl)carbodiimide added thereto were gradually heated to normal room temperature and stirred at the same temperature for 12 hours. The resultant reaction solution was concentrated under a reduced pressure. The residue of this concentration was neutralized by addition of an aqueous potassium carbonate solution and extracted with chloroform. The chloroform layer was dried over anhydrous magnesium sulfate and then distilled. The residue of this distillation was refined by silica gel column chromatography to obtain 725 mg of 5-(3-phenylindolin-1-ylcarbonyl)-4,5,6,7-tetrahydrobenzimidazole (82.5%) as an epimer mixture.

$^1$H-NMR (δ ppm, CDC13, 270 MHz): 2.00–2.30 (2H, m), 2.50–3.20 (5H, m), 4.00–4.10 (1H, m), 4.50–4.70 (2H, m), 6.90–7.10 (2H, m), 7.10–7.40 (6H, m), 7.49 (0.5H, s), 7.51 (0.5H, s), 8.34 (1H, d)

HPLC (Column; CAPCELL PAK C18 SG120, 4.6 mm in Diam.×150 mm, eluting solvent; 50 mM (NH$_4$)$_2$HPO$_4$:MeOH=1:1, flow rate; 0.8 ml/minute, temperature; 35° C.): retention time 33.20 minutes and 35.70 minutes

EXAMPLE 20

5-[{3-3-(Hydroxyphenyl)indolin-1-ylcarbonyl}]-4,5,6,7-tetrahydrobenzimidazole

A mixture of 1.99 g of hydrochloride (racemic form) of 4,5,6,7-tetrahydrobenzimidazole-5-carboxylic acid, 0.15 ml of dimethyl formamide and 20 ml of thionyl chloride was refluxed for three hours. The resultant reaction solution was distilled to dryness under a reduced pressure. The residue consequently formed was added to a solution of 2.07 g of (+)-3-(3-hydroxyphenyl)indoline in 75 ml of tetrahydrofuran. This reaction solution was stirred at room temperature for 12 hours, then weakly alkalinized by addition of the saturated aqueous sodium bicarbonate solution, and extracted with chloroform. The chloroform layer was dried over anhydrous magnesium sulfate and then distilled. The residue was refined by silica gel column chromatography to obtain 2.00 g of 5-[{3-(3-hydroxyphenyl)indolin-1-ylcarbonyl}]-4,5,6,7-tetrahydrobenzimidazole (56.8%) as an epimer mixture.

$^1$H-NMR (δ ppm, DMSO-d6, 270 MHz): 1.60–1.85 (1H, m), 1.95–2.25 (1H, m), 2.48–3.15 (5H, m), 4.00–4.20 (1H, m), 4.52–4.75 (2H, m), 6.50–6.70 (3H, m), 6.85–7.30 (4H, m), 7.41 (0.5H, s), 7.42 (0.5H, s), 8.21 (1H, d), 9.42 (1H, brs), 11.70 (1H, brs)

HPLC (Column; CAPCELL PAK C18 SG120, 4.6 mm in Diam.×150 mm, eluting solvent; 50 mM (NH$_4$)$_2$HPO$_4$:MeOH=1:1, flow rate; 0.8 ml/minute, temperature; 25° C.): retention time 13.20 minutes and 14.72 minutes

EXAMPLE 21

5-[3-(3-methoxyphenyl)indolin-1-ylcarbonyl]-4,5,6,7-tetrahydrobenzimidazole

By following the procedure of Example 20 substantially faithfully while using 2.34 g of (+)-3-(3-methoxyphenyl) indoline in the place of (+)-3-(3-hydroxyphenyl)indoline, 1.90 g of 5-[3-(3-methoxyphenyl)indolin-1-ylcarbonyl]-4,5,6,7-tetrahydrobenzimidazole (48.8%) was obtained as an epimer mixture from 2.11 g of the hydrochloride (racemic form) of 4,5,6,7-tetrahydrobenzimidazole-5-carboxylic acid.

$^1$H-NMR (δ ppm, DMSO-d6, 270 MHz): 1.60–1.85 (1H, m), 1.95–2.25 (1H, m), 2.48–3.15 (5H, m), 3.72 (3H, s), 4.05–4.20 (1H, m), 4.52–4.80 (2H, m), 6.70–6.85 (3H, m), 6.90–7.05 (2H, m), 7.15–7.30 (2H, m), 7.40 (0.5H, s), 7.41 (0.5H, s), 8.21 (1H, d), 11.70 (1H, brs)

EXAMPLE 22

Optically active 5-(3-phenylindolin-1-ylcarbonyl)-4,5,6,7-tetrahydrobenzimidazole By recrystallizing 3.30 g of 5-(3-phenylindolin-1-yl carbonyl)-4,5,6,7-tetrahydrobenzimidazole obtained as an epimer mixture in Example 19 from 99 ml of ethyl acetate, 1.05 g of optically active 5-(3-phenylindolin-1-ylcarbonyl)-

4,5,6,7-tetrahydrobenzimidazole (31.8%) was obtained. This compound was identical with the compound of Referential Example 3.

$^1$H-NMR (δ ppm, CDC13, 270 MHz): 1.9–2.2 (2H, m), 2.5–3.2 (5H, m), 4.0–4.1 (1H, m), 4.5–4.7 (2H, m), 6.9–7.1 (2H, m), 7.1–7.4 (6H, m), 7.53 (1H, s), 8.34 (1H, d)

HPLC (Column; CAPCELL PAK C18 SG120, 4.6 mm in Diam.×150 mm, eluting solvent; 50 mM $(NH_4)_2HPO_4$:MeOH=1:1, flow rate; 0.8 ml/minute, temperature; 35° C.): retention time 35.70 minutes HPLC (Column; CHIRALCEL OD, 4.6 mm in Diam.×50 mm, produced by Daicel Kagaku Kogyo K.K., eluting solvent; n-hexane:isopropyl alcohol=6:1, flow rate; 0.8 ml/minute); retention time 19.24 minutes

EXAMPLE 23

Optically active 5-[3-3-(hydroxyphenyl)indolin-1-ylcarbonyl]-4,5,6,7-tetrahydrobenzimidazole By following the procedure of Example 22 substantially faithfully while using 549 mg of the 5-[3-(3-hydroxyphenyl)-indolin-1-ylcarbonyl]-4,5,6,7-tetrahydrobenzimidazole obtained as an epimer mixture in Example 20 in the place of the 5-(3-phenylindolin-1-ylcarbonyl)-4,5,6,7-tetrahydrobenzimidazole obtained as an epimer mixture in Example 19 and changing the solvent for recrystallization to ethanol, 110 mg of optically active 5-[3-(3-hydroxyphenyl)indolin-1-ylcarbonyl]-4,5,6,7-tetrahydrobenzimidazole (20.0%) was obtained.

$^1$H-NMR (δ ppm, DMSO-d6, 270 MHz): 1.7–1.9 (1H, m), 1.9–2.1 (1H, m), 2.5–2.6 (2H, m), 2.7–2.8 (2H, m), 2.9–3.1 (1H, m), 4.0–4.1 (1H, m), 4.5–4.7 (2H, m), 6.5–6.7 (3H, m), 6.9–7.1 (2H, m), 7.0–7.3 (2H, m), 7.41 (1H, s), 8.21 (1H, d), 9.40 (1H, brs), 11.6 (1H, brs)

HPLC (Column; CAPCELL PAK C18 SG120, 4.6 mm in Diam.×150 mm, eluting solvent; 50 mM $(NH_4)_2HPO_4$:MeOH=1:1, flow rate; 0.8 ml/minute, temperature; 25° C.): retention time 13.20 minutes Example 24

Optically active 5-[3-(3-methoxyphenyl)indolin-1-ylcarbonyl]-4,5,6,7-tetrahydrobenzimidazole By following the procedure of Example 22 substantially faithfully while using 1010 mg of the 5-[3-(3-methoxyphenyl)-indolin-1-ylcarbonyl]-4,5,6,7-tetrahydrobenzimidazole obtained as an epimer mixture in Example 21 in the place of the 5-(3-phenylindolin-1-ylcarbonyl)-4,5,6,7-tetrahydrobenzimidazole obtained as an epimer mixture in Example 19 and changing the solvent for recrystallization to ethanol, 426 mg of optically active 5-[3-(3-methoxyphenyl)indolin-1-ylcarbonyl]-4,5,6,7-tetrahydrobenzimidazole (42.2%) was obtained.

$^1$H-NMR (δ ppm, DMSO-d6, 270 MHz): 1.7–1.9 (1H, m), 1.9–2.1 (1H, m), 2.5–2.7 (2H, m), 2.7–2.8 (2H, m), 2.9–3.5 (1H, m), 3.7 (3H, s), 4.0–4.2 (1H, m), 4.6–4.8 (2H, m), 6.7–6.9 (3H, m), 6.9–7.0 (2H, m), 7.1–7.3 (2H, m), 7.43 (1H, s), 8.21 (1H, d), 11.6 (1H, brs)

EXAMPLE 25

Optically active 5-[3-(3-hydroxyphenyl)indolin-1-yl carbonyl]-4,5,6,7-tetrahydrobenzimidazole In 9 ml of chloroform, 300 mg of the optically active 5-[3-(3-methoxyphenyl]indolin-1-ylcarbonyl]-4,5,6,7-tetrahydrobenzimidazole obtained in Example 24 was solved. This solution and 3.1 ml of a 1.0M dichloromethane solution of boron tribromide added thereto in a stream of argon at −78° C. were together stirred at −78° C. for three hours and further at normal room temperature for three hours. The resultant reaction solution was poured into ice water, neutralized with an aqueous sodium hydrogen carbonate solution, and then extracted with a mixed solution of chloroform and ethanol. The organic layer was dried over magnesium sulfate and then distilled. The residue of the distillation was refined by silica gel column chromatography to obtain 220 mg of optically active 5-[3-(3-hydroxyphenyl)indolin-1-ylcarbonyl]-4,5,6,7-tetrahydrobenzimidazole (76.1%).

The $^1$H-NMR and the HPLC of this compound were identical with those of the compound of Example 23.

Example 26

Optically active 5-[5-fluoro-3-(2-methoxyphenyl)indolin-1-ylcarbonyl]-4,5,6,7-tetrahydrobenzimidazole By following the procedure of Example 19 substantially faithfully while using 0.30 g of (+)-5-fluoro-3-(2-methoxyphenyl)indoline in the place of (+)-3-phenylindoline, 0.25 g of 5-[5-fluoro-3-(2-methoxyphenyl)indolin-1-ylcarbonyl]-4,5,6,7-tetrahydrobenzimidazole (52.1%) was obtained as an epimer mixture. By further recrystallizing this compound from a mixed solution of ethyl acetate and hexane in the same manner as in the procedure of Example 22, 0.1 g of optically active 5-[5-fluoro-3-(2-methoxyphenyl)indolin-1-ylcarbonyl]-4,5,6,7-tetrahydrobenzimidazole was obtained.

Example 27

Optically active 5-[6-methoxycarbonyl-3-(4-methoxyphenyl)indolin-1-ylcarbonyl]-4,5,6,7-tetrahydrobenzimidazole By following the procedure of Example 19 substantially faithfully while using 0.2 g of (+)-6-methoxycarbonyl-3-(4-methoxyphenyl)indoline in the place of (+)-3-phenylindoline, 0.2 g of 5-[6-methoxycarbonyl-3-(4-methoxyphenyl)indolin-1-ylcarbonyl]-4,5,6,7-tetrahydrobenzimidazole (66.7%) was obtained. By further recrystallizing this compound from a mixed solution of ethyl acetate and hexane in the same manner as in the procedure of Example 22, 0.07 g of optically active 5-[6-methoxycarbonyl-3-(4-methoxyphenyl)indolin-1-ylcarbonyl]-4,5,6,7-tetrahydrobenzimidazole was obtained.

INDUSTRIAL APPLICABILITY

By the method of production of this invention, a 3-arylindoline compound which is an intermediate for the production of a 1-acyl-3-arylindoline compound, i.e. the 5-$HT_3$ receptor antagonist, can be produced advantageously on a commercial scale without entraining decomposition of an indole compound as the raw material, exposing the reaction device to corrosion or breakage, or inducing any pollution of the environment with a zinc compound. An optically active 3-arylindoline compound can be efficiently produced and further an optically active 1-acyl-3-arylindoline compound can be easily produced by using an optically active 1-acyl-3-arylindole compound of this invention.

We claim:

1. Method for producing a 3-(hetero)aryl indoline compound of formula (2)

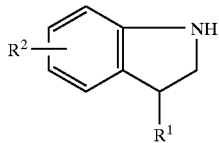

(2)

wherein R¹ is an optionally substituted phenyl group or aromatic heterocyclic group and R² is a hydrogen atom, a halogen atom, a lower alkyl group, a hydroxy group, a lower alkoxy group, a carbamoyl group, or a lower alkoxycarbonyl group, which comprises subjecting a 1-acyl-3-(hetero)aryl indole compound of formula (6)

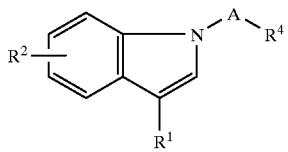

(6)

wherein R¹ and R² are the same as defined above, R⁴ is an optionally substituted linear, branched, or cyclic alkyl group, aryl group, or aromatic or saturated heterocyclic group, and A is a carbonyl group or sulfonyl group, which can be formed by condensing a 3-(hetero)aryl indole compound of formula (4)

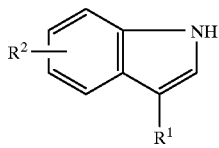

(4)

wherein R¹ and R² are the same as defined above, with an organic acid of formula (5)

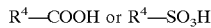

R⁴—COOH or R⁴—SO₃H      (5)

wherein R⁴ is the same as defined above, or an acid halide or acid anhydride thereof, to a reduction reaction to form a 1-acyl-3-(hetero)aryl indoline compound of formula (7)

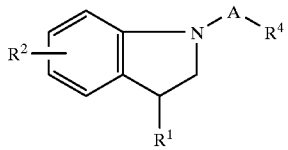

(7)

wherein R¹, R², R⁴ and A are the same as defined above, and hydrolyzing the 1-acyl-3-(hetero)aryl indoline compound of formula (7).

2. Method of claim 1 wherein said organic acid is acetic acid, propionic acid, butyric acid, mandelic acid, campho- carboxylic acid, cyclohexane carboxylic acid, benzoic acid, toluic acid, fluorobenzoic acid, chlorobenzoic acid, methoxybenzoic acid, carbamoyl benzoic acid, methoxycarbonyl benzoic acid, naphthoic acid, furan carboxylic acid, thiophene carboxylic acid, pyridine carboxylic acid, amino group protected amino acid, p-toluene sulfonic acid, or camphor sulfonic acid.

3. Method of claim 1 wherein said organic acid is an optically active organic acid of formula (9)

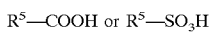

R⁵—COOH or R⁵—SO₃H      (9)

wherein R⁵ is an optionally substituted linear, branched, or cyclic alkyl group, aryl group, or aromatic or saturated heterocyclic group possessed of asymmetry.

4. Method of claim 3 wherein said optically active organic acid is an optically active mandelic acid, camphocarboxylic acid, amino group protected amino acid, or 10-camphor sulfonic acid.

5. Method of claim 4 wherein said amino group protected amino acid is N-tosyl-D-proline or N-trifluoroacetyl-D-proline.

6. Optically active 1-acyl-3-(hetero)aryl indole compound of formula (10)

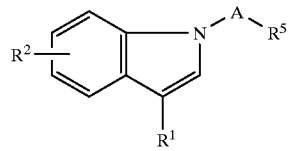

(10)

wherein R¹ is an optionally substituted phenyl group or aromatic heterocyclic group, R² is a hydrogen atom, a halogen atom, a lower alkyl group, a hydroxy group, a lower alkoxy group, a carbamoyl group, or a lower alkoxycarbonyl group, R⁵ is an optionally substituted linear, branched, or cyclic alkyl group, aryl group, or aromatic or saturated heterocyclic group possessed of asymmetry, and A is a carbonyl group or sulfonyl group.

7. Optically active 1-acyl-3-(hetero)aryl indole compound of claim 6 which is an optically active 1-D-prolyl-3-(hetero)aryl indole compound of formula (13)

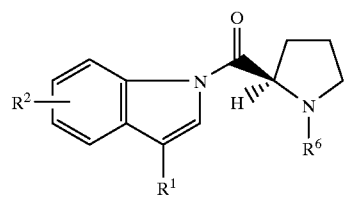

(13)

wherein R¹ and R² are the same as defined above and R⁶ is a protective group for an amino group.

8. Optically active 1-D-prolyl-3-(hetero)aryl indole compound of claim 7 wherein R⁶ is a tosyl group or a trifluoroacetyl group.

9. Optically active 1-acyl-3-(hetero)aryl indole compound of claim 7 which is a 3-phenyl-1-(N-tosyl-D-prolyl) indole,
a 3-(3-methoxyphenyl)-1-(N-tosyl-D-prolyl) indole,
a 3-(3-hydroxyphenyl)-1-(N-tosyl-D-prolyl) indole, or
a 3-phenyl-1-(N-trifluoroacetyl-D-prolyl) indole.

10. Optically active 1-acyl-3-(hetero)aryl indoline compound of formula (11)

(11)

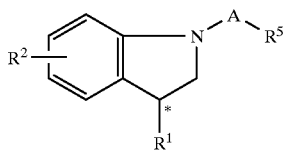

wherein R¹ is an optionally substituted phenyl group or aromatic heterocyclic group, R² is a hydrogen atom, a halogen atom, a lower alkyl group, a hydroxy group, a lower alkoxy group, a carbamoyl group, or a lower alkoxycarbonyl group, R⁵ is an optionally substituted linear, branched, or cyclic alkyl group, aryl group, or aromatic or saturated heterocyclic group possessed of asymmetry, A is a carbonyl group or sulfonyl group, and * indicates the asymmetric center of an optically active compound.

11. Optically active 1-acyl-3-(hetero)aryl indoline compound of claim 10 which is an optically active 1-D-prolyl-3-(hetero)aryl indoline compound of formula (14)

(14)

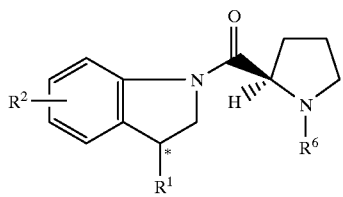

wherein R¹, R² and * are the same as defined above and R⁶ is a protective group for an amino group.

12. Optically active 1-D-prolyl-3-(hetero) aryl indoline compound of claim 11 wherein R⁶ is a tosyl group or a trifluoroacetyl group.

13. Optically active 1-acyl-3-(hetero)aryl indoline compound of claim 11 which is an optically active 3-phenyl-1-(N-tosyl-D-prolyl) indoline, an optically active 3-(3-methoxyphenyl)-1-(N-tosyl-D-prolyl) indoline, an optically active 3-(3-hydroxyphenyl)-1-(N-tosyl-D-prolyl) indoline, or an optically active 3-phenyl-1-(N-trifluoroacetyl-D-prolyl) indoline.

14. Method for producing an optically active 1-acyl-3-(hetero)aryl indoline compound of formula (15)

(15)

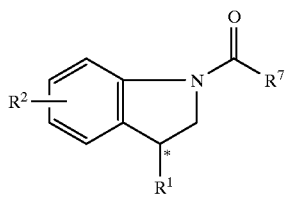

wherein R¹ is an optionally substituted phenyl group or aromatic heterocyclic group, R² is a hydrogen atom, a halogen atom, a lower alkyl group, a hydroxy group, a lower alkoxy group, a carbamoyl group, or a lower alkoxycarbonyl group, * indicates the asymmetric center of an optically active compound, and R⁷ is a 4,5,6,7-tetrahydro benzimidazole-5 or 6-yl group of the formula

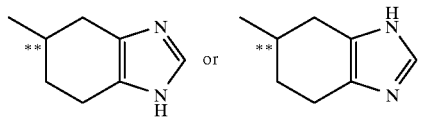

wherein ** indicates the asymmetric center of an optically active compound, independently of *, which comprises subjecting an optically active 1-acyl-3-(hetero)aryl indole compound of formula (10)

(10)

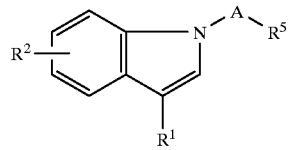

wherein R¹ and R² are the same as defined above, R⁵ is an optionally substituted linear, branched, or cyclic alkyl group, aryl group, or aromatic or saturated heterocyclic group possessed of asymmetry, and A is a carbonyl group or sulfonyl group, which can be formed by condensing a 3-(hetero)aryl indole compound of formula (4)

(4)

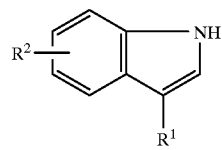

wherein R¹ and R² are the same as defined above, with an optically active organic acid of formula (9)

R⁵—COOH or R⁵—SO₃H    (9)

wherein R⁵ is the same as defined above, or an acid halide or acid anhydride thereof, to a reduction reaction to form an optically active 1-acyl-3-(hetero)aryl indoline compound of formula (11)

(11)

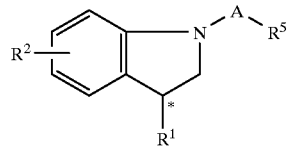

wherein R¹, R², R⁵, A and are the same as defined above, hydrolyzing the optically active 1-acyl-3-(hetero)aryl indoline compound of formula (11) to form an optically active 3-(hetero)aryl indoline compound of formula (8)

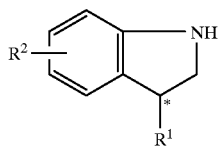
(8)

wherein R¹, R² and * are the same as defined above, condensing the optically active 3-(hetero)aryl indoline compound of formula (8) with a carboxylic acid compound of the formula

R³—COOH wherein R³ is a 4,5,6,7-tetrahydro benzimidazole-5 or 6-yl group of the formula

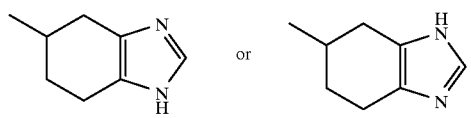

which is a racemic substance, to form an epimer mixture of a 1-acyl-3-(hetero)aryl indoline compound of formula (15)

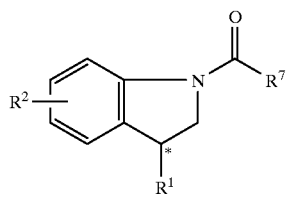
(15)

wherein R¹, R², R⁷ and * are the same as defined above, and fractionally recrystallizing said epimer mixture from an organic solvent.

15. Method of claim 14 wherein said optically active compound of formula (15) is an optically active 5-(3-phenyl indolin-1-yl carbonyl)-4,5,6,7-tetrahydro benzimidazole which is produced by condensing a 3-phenyl indole with an N-tosyl-D-proline to form a 3-phenyl-1-(N-tosyl-D-prolyl) indole, reducing the resulting condensation product to form an optically active 3-phenyl-1-(N-tosyl-D-prolyl) indoline, hydrolyzing the resulting product of reduction to form a (+)-3-phenyl indoline, condensing the resulting product of hydrolysis with a 4,5,6,7-tetrahydro benzimidazole-5-carboxylic acid as a racemic substance to form an epimer mixture of a 5-(3-phenyl indolin-1-yl carbonyl)-4,5,6,7-tetrahydro benzimidazole, and recrystallizing the epimer mixture.

16. Method which comprises reducing a 1-acyl-3-(hetero) aryl indole compound of formula (6)

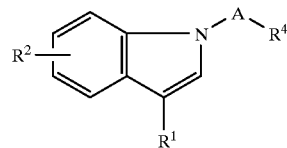
(6)

wherein R¹ is an optionally substituted phenyl group or aromatic heterocyclic group, R² is a hydrogen atom, a halogen atom, a lower alkyl group, a hydroxy group, a lower alkoxy group, a carbamoyl group, or a lower alkoxycarbonyl group, R⁴ is an optionally substituted linear, branched, or cyclic alkyl group, aryl group, or aromatic or saturated heterocyclic group, and A is a carbonyl group or sulfonyl group, in the presence of a reducing catalyst under neutral or weakly acidic conditions to form a 1-acyl-3-(hetero)aryl indoline compound of formula (7)

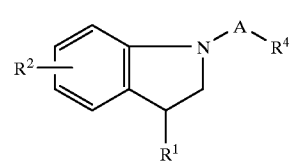
(7)

wherein R¹, R², R⁴ and A are the same as defined above.

17. Method of claim 16 wherein the 1-acyl-3-(hetero)aryl indole compound of formula (6) is formed by condensing a 3-(hetero)aryl indole compound of formula (4)

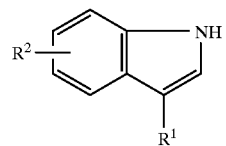
(4)

wherein R¹ and R² are the same as defined above, with an organic acid of formula (5)

R⁴—COOH or R⁴—SO₃H         (5)

wherein R⁴ is the same as defined above, or an acid halide or acid anhydride thereof.

18. Method of claim 17 wherein said organic acid is acetic acid, propionic acid, butyric acid, mandelic acid, camphocarboxylic acid, cyclohexane carboxylic acid, benzoic acid, toluic acid, fluorobenzoic acid, chlorobenzoic acid, methoxybenzoic acid, carbamoyl benzoic acid, methoxycarbonyl benzoic acid, naphthoic acid, furan carboxylic acid, thiophene carboxylic acid, pyridine carboxylic acid, amino group protected amino acid, p-toluene sulfonic acid, or camphor sulfonic acid.

19. Method of claim 17 wherein said organic acid is an optically active organic acid of formula (9)

R⁵—COOH or R⁵—SO₃H         (9)

wherein R⁵ is an optionally substituted linear, branched, or cyclic alkyl group, aryl group, or aromatic or saturated heterocyclic group possessed of asymmetry.

20. Method of claim 19 wherein said optically active organic acid is an optically active mandelic acid, camphocarboxylic acid, amino group protected amino acid, or 10-camphor sulfonic acid.

21. Method of claim 20 wherein said amino group protected amino acid is N-tosyl-D-proline or N-trifluoroacetyl-D-proline.

22. Method of claim 16 wherein the 1-acyl-3-(hetero) aryl indoline compound of formula (7) is hydrolyzed to form a 3-(hetero)aryl indoline compound of formula (2)

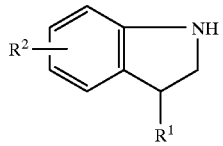

(2)

wherein $R^1$ and $R^2$ are the same as defined above.

23. Method which comprises reducing an optically active 1-acyl-3-(hetero)aryl indole compound of formula (10)

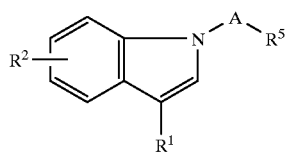

(10)

wherein $R^1$ is an optionally substituted phenyl group or aromatic heterocyclic group, $R^2$ is a hydrogen atom, a halogen atom, a lower alkyl group, a hydroxy group, a lower alkoxy group, a carbamoyl group, or a lower alkoxycarbonyl group, $R^5$ is an optionally substituted linear, branched, or cyclic alkyl group, aryl group, or aromatic or saturated heterocyclic group possessed of asymmetry, and A is a carbonyl group or sulfonyl group, in the presence of a reducing catalyst under neutral or weakly acidic conditions to form an optionally active 1-acyl-3-(hetero)aryl indoline compound of formula (11)

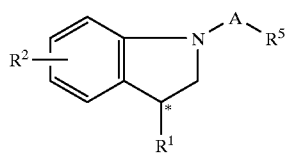

(11)

wherein $R^1$, $R^2$, $R^5$ and A are the same as defined above and * indicates the asymmetric center of an optically active compound.

24. Method of claim 23 wherein the optically active 1-acyl-3-(hetero)aryl indole compound of formula (10) is formed by condensing a 3-(hetero)aryl indole compound of formula (4)

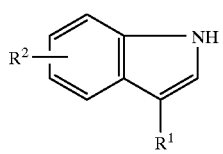

(4)

wherein $R^1$ and $R^2$ are the same as defined above, with an optically active organic acid of formula (9)

$$R^5\text{—COOH or } R^5\text{—SO}_3\text{H} \tag{9}$$

wherein $R^5$ is the same as defined above, or an acid halide or acid anhydride thereof.

25. Method of claim 23 wherein the optically active 1-acyl-3-(hetero)aryl indoline compound of formula (11) is hydrolyzed to form an optically active 3-(hetero)aryl indoline compound of formula (8)

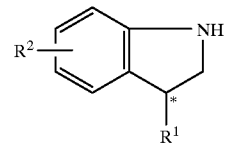

(8)

wherein $R^1$, $R^2$ and * are the same as defined above, the optically active 3-(hetero)aryl indoline compound of formula (8) is condensed with a carboxylic acid compound of the formula $$R^3\text{—COOH}$$

wherein $R^3$ is a 4,5,6,7-tetrahydro benzimidazole-5 or 6-yl group of the formula

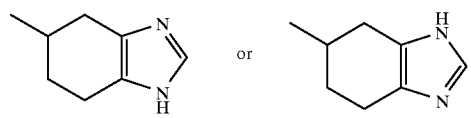

which is a racemic substance, to form an epimer mixture of a 1-acyl-3-(hetero)aryl indoline compound of formula (15)

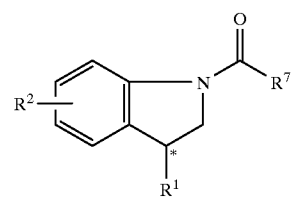

(15)

wherein $R^1$, $R^2$ and * are the same as defined above and $R^7$ is a 4,5,6,7-tetrahydro benzimidazole-5 or 6-yl group of the formula

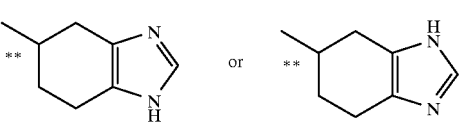

wherein ** indicates the asymmetric center of an optically active compound, independently of *, and said epimer mixture is fractionally recrystallized from an organic solvent to form an optically active 1-acyl-3-(hetero)aryl indoline compound of formula (15).

* * * * *